United States Patent
Shamain et al.

(10) Patent No.: US 11,660,008 B2
(45) Date of Patent: May 30, 2023

(54) ARTERIAL PULSE MEASUREMENT

(71) Applicant: Nokia Technologies Oy, Espoo (FI)

(72) Inventors: Durgaprasad Shamain, San Jose, CA (US); Klaus Doppler, Albany, CA (US); Swetha Muniraju, Burlingame, CA (US); Eric Torkildson, San Francisco, CA (US)

(73) Assignee: Nokia Technologies Oy, Espoo (FI)

( * ) Notice: Subject to any disclaimer, the term of this patent is extended or adjusted under 35 U.S.C. 154(b) by 1029 days.

(21) Appl. No.: 15/869,587

(22) Filed: Jan. 12, 2018

(65) Prior Publication Data

US 2018/0206743 A1 Jul. 26, 2018

(30) Foreign Application Priority Data

Jan. 20, 2017 (EP) ..................... 17152323

(51) Int. Cl.
*A61B 5/021* (2006.01)
*A61B 5/0285* (2006.01)
(Continued)

(52) U.S. Cl.
CPC ........ *A61B 5/02125* (2013.01); *A61B 5/0059* (2013.01); *A61B 5/024* (2013.01);
(Continued)

(58) Field of Classification Search
CPC .... G01S 13/10; G01S 2013/468; G01S 15/42; G01S 15/10; G01S 13/00; G01S 17/42;
(Continued)

(56) References Cited

U.S. PATENT DOCUMENTS

| 7,916,066 B1 * | 3/2011 | Osterweil | A61B 5/1117 |
| | | | 342/28 |
| 9,011,346 B2 * | 4/2015 | Wiard | A61B 5/0285 |
| | | | 600/526 |

(Continued)

FOREIGN PATENT DOCUMENTS

| CN | 101247757 A | 8/2008 |
| CN | 102178516 A | 9/2011 |

(Continued)

OTHER PUBLICATIONS

N. V. Rivera, S. Venkatesh, C. Anderson and R. M. Buehrer, "Multi-target estimation of heart and respiration rates using ultra wideband sensors," 2006 14th European Signal Processing Conference, Florence, 2006, pp. 1-6. (Year: 2006).*

(Continued)

*Primary Examiner* — Catherine B Kuhlman
*Assistant Examiner* — Abid A Mustansir
(74) *Attorney, Agent, or Firm* — Mendelsohn Dunleavy, P.C.; Steve Mendelsohn; Yuri Gruzdkov (57) ABSTRACT

A method and a system for determining an in vivo transit distance and a corresponding transit time for an arterial pulse. An example system comprises a radar receiver connected to a processor to perform time-resolved measurements of reflections of wave pulses and to spectrally filter the reflections to select spectral components associated with the arterial pulse. The resulting signal samples are then organized into groups corresponding to different wave pulses, and the groups are processed to identify samples corresponding to a first arterial pulse point and a second arterial pulse point on the body of a subject, and the identified samples are further processed to determine the in vivo transit distance and the corresponding transit time for the arterial pulse. In some embodiments, a collection of arterial pulse points detected by the measurements may be (Continued)

mapped onto a reference constellation for a more-accurate determination of the in vivo transit distance.

16 Claims, 3 Drawing Sheets

(51) Int. Cl.
| | |
|---|---|
| *A61B 5/00* | (2006.01) |
| *A61B 5/0507* | (2021.01) |
| *A61B 5/02* | (2006.01) |
| *A61B 5/024* | (2006.01) |

(52) U.S. Cl.
CPC ........ *A61B 5/02007* (2013.01); *A61B 5/0285* (2013.01); *A61B 5/02108* (2013.01); *A61B 5/0507* (2013.01); *A61B 5/725* (2013.01); *A61B 5/7253* (2013.01)

(58) Field of Classification Search
CPC .......... G01S 15/88; G01S 17/10; G01S 17/88; A61B 5/05; A61B 8/06; A61B 5/02125; A61B 5/0059; A61B 5/02007; A61B 5/02108; A61B 5/024; A61B 5/0285; A61B 5/0507; A61B 5/725; A61B 5/7253; A61B 5/4887; A61B 5/02416; A61B 5/02427
See application file for complete search history.

(56) References Cited

U.S. PATENT DOCUMENTS

| | | | | |
|---|---|---|---|---|
| 2006/0287600 | A1* | 12/2006 | McEowen .......... | A61B 5/14535 600/481 |
| 2008/0045847 | A1* | 2/2008 | Farag ................. | A61B 5/02055 600/500 |
| 2011/0040176 | A1* | 2/2011 | Razansky ............... | A61B 5/05 600/425 |
| 2013/0184595 | A1* | 7/2013 | Mukkamala ....... | A61B 5/02125 600/485 |
| 2015/0257653 | A1* | 9/2015 | Hyde ................... | A61B 5/0077 600/473 |
| 2016/0228010 | A1* | 8/2016 | Kim ...................... | A61B 5/021 |
| 2016/0327635 | A1* | 11/2016 | Scheim ................ | G01S 7/4815 |
| 2016/0338599 | A1* | 11/2016 | DeBusschere ....... | A61B 5/0295 |

FOREIGN PATENT DOCUMENTS

| | | |
|---|---|---|
| CN | 102421371 A | 4/2012 |
| CN | 102551686 A | 7/2012 |
| CN | 105792742 A | 7/2016 |
| WO | 2007/023426 A2 | 3/2007 |
| WO | 2009/136341 A2 | 11/2009 |
| WO | 2015/118544 A1 | 8/2015 |
| WO | 2016/009315 A1 | 1/2016 |

OTHER PUBLICATIONS

Guillén, Antonio & Girbau, David & Villarino, R.. (2010). Analysis of vital signs monitoring using an IR-UWB radar. Progress In Electromagnetics Research. 100. 265-284. 10.2528/PIER09120302. (Year: 2010).*

L. Ren, H. Wang, K. Naishadham, O. Kilic and A. E. Fathy, "Phase-Based Methods for Heart Rate Detection Using UWB Impulse Doppler Radar," in IEEE Transactions on Microwave Theory and Techniques, vol. 64, No. 10, pp. 3319-3331, Oct. 2016, doi: 10.1109/TMTT.2016.2597824. (Year: 2016).*

Michahelles et al., "Less Contact: Heart-Rate Detection Without Even Touching The User", Eighth International Symposium on Wearable Computers, Oct. 31-Nov. 3, 2004, 4 pgaes.

Zito et al., "Wearable System-on-a-Chip UWB Radar for Contactless Cardiopulmonary Monitoring: Present Status", 30th Annual International Conference of the IEEE Engineering in Medicine and Biology Society, Aug. 20-24, 2008, pp. 5274-5277.

"Physiology Of The Cardiovascular System", Nurseslearning, Retrieved on Jan. 16, 2018, Webpage available at : https://www.nurseslearning.com/courses/nrp/NRP-1616/Section5/p01.html.

"Moens-Korteweg Equation", Wikipedia, Retrieved on Jan. 16, 2018, Webpage available at : https://en.wikipedia.org/wiki/Moens%E2%80%93Korteweg_equation.

Lu et al., "Microwave Noncontact Measurement of Pulse Wave Velocity for Healthcare Applications", IEEE 11th Annual Wireless and Microwave Technology Conference, Apr. 12-13, 2010, pp. 1-5.

Lu et al., "Experimental Demonstration of Noncontact Pulse Wave Velocity Monitoring Using Multiple Doppler Radar Sensors", Annual International Conference of the IEEE Engineering in Medicine and Biology Society, Aug. 31-Sep. 4, 2010, pp. 5010-5013.

Extended European Search Report received for corresponding European Patent Application No. 17152323.6, dated Aug. 7, 2017, 7 pages.

"Radar Basics—Part 1", EE Times, Retrieved on Jan. 17, 2018, Webpage available at : https://www.eetimes.com/document.asp?doc_id=1278779.

"The Cardiac Exam: Palpation" Retrieved on Feb. 8, 2018, • http://casemed.case.edu/cardiacexam/palpate.htm.

Office action received for corresponding Chinese Patent Application No. 201810055674.X, dated Jun. 1, 2020, 12 pages of office action and 4 pages of Translation available.

Second Office Action for corresponding Chinese application No. 201810055674.X; dated Feb. 5, 2021 (7 pages).

* cited by examiner

ARTERIAL PULSE MEASUREMENT

TECHNOLOGICAL FIELD

Embodiments of the present innovation relate to arterial pulse measurement. In particular, embodiments of the present innovation relate to measurement of parameters for determining a pulse wave velocity of an arterial pulse.

BACKGROUND

In an animal, for example a human, a heart circulates blood through a circulatory system comprising arteries for directing blood from the heart and veins for returning blood to the heart. The pumping action of the heart creates a pressure wave that travels along the blood filled arteries. This pressure wave may be detected as a volume change or pulse at an arterial pulse point. The transit time of the pressure wave between two points or velocity of the pressure wave, the pulse wave velocity, provide useful information on the health of the arteries.

BRIEF SUMMARY

According to various, but not necessarily all, embodiments of the innovation there is provided a method comprising: at a processor, determining an in vivo transit distance for an arterial pulse between a first arterial pulse point and a second arterial pulse point using a first distance measured to the first arterial pulse point and a second distance measured to a second arterial pulse point; and at the processor, determining a transit time for an arterial pulse between the first arterial pulse point and the second arterial pulse point, based on one or more transmitted signals reflected from the first arterial pulse point and from one or more transmitted signals reflected from the second arterial pulse point. The transmitted signals may be detecting and ranging wave pulses.

According to various, but not necessarily all, embodiments of the innovation there is provided examples as claimed in the appended claims.

BRIEF DESCRIPTION

For a better understanding of various examples that are useful for understanding the detailed description, reference will now be made by way of example only to the accompanying drawings in which.

DETAILED DESCRIPTION

A new method 100 and a new system 202 is described for determining in vivo transit distance for an arterial pulse and for determining or enabling determination of the pulse wave velocity.

Figure 1:
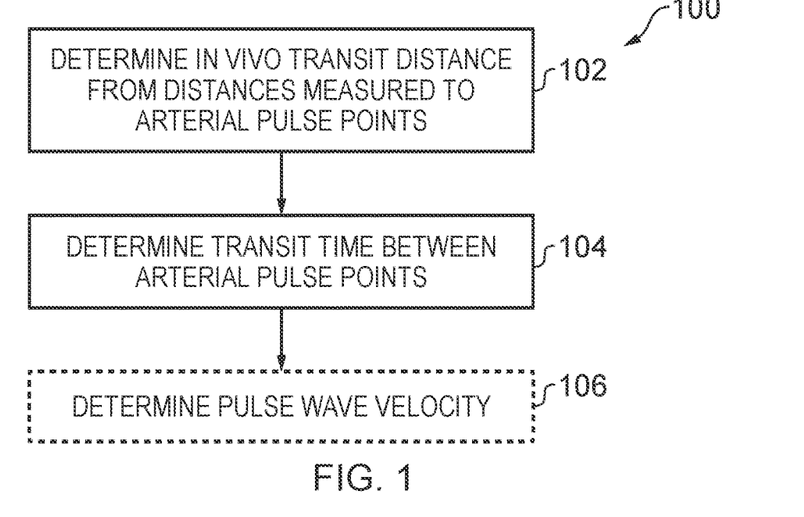
FIG. 1 illustrates an example of a method for determining a transit time of an arterial pulse between arterial pulse points.

FIG. 1 illustrates an example of a method 100 for determining a transit time of an arterial pulse from a first arterial pulse point $12_1$ to a second arterial pulse point $12_2$. In some examples, the first arterial pulse point $12_1$ and the second arterial pulse point $12_2$ are predetermined arterial pulse points. In other examples, the first arterial pulse point $12_1$ and the second arterial pulse point 122 are arbitrary arterial pulse points.

Figure 2A:
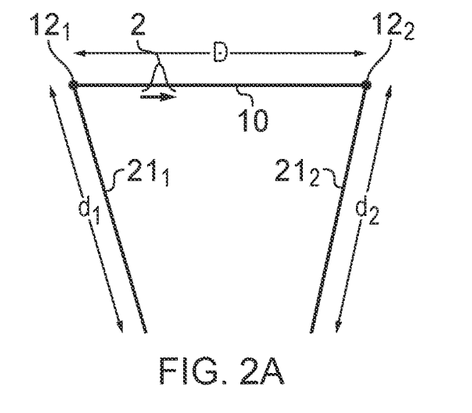
FIGS. 2A and 2B illustrate reflection of transmitted signals from arterial pulse points.
Figure 2B:
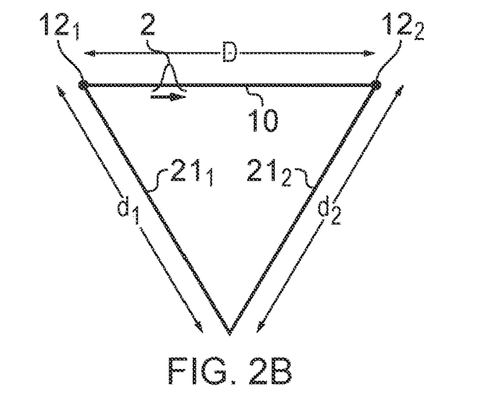

The method 100 refers to in vivo transit distance D along an artery 10, an arterial pulse 2, a first arterial pulse point $12_1$, a second arterial pulse point $12_2$, a first distance $d_1$ to the first arterial pulse point $12_1$ and a second distance $d_2$ to a second arterial pulse point $12_2$, one or more transmitted signals reflected $21_1$ from the first arterial pulse point $12_1$ and one or more transmitted signals reflected $21_2$ from the second arterial pulse point $12_2$, which are illustrated by example in FIGS. 2A and 2B. The in vivo transit distance D is the distance travelled by the arterial pulse 2 within a subject's body along the subject's arterial system between two arterial pulse points, in this example the first arterial pulse point $12_1$ and the second arterial pulse point $12_2$.

The first distance $d_1$ to the first arterial pulse point $12_1$ may be a distance measured from a receiver of the one or more transmitted signals reflected $21_1$ from the first arterial pulse point $12_1$. The second distance $d_2$ to the second arterial pulse point $12_2$ may be a distance from a receiver of the one or more transmitted signals reflected $21_2$ from the second arterial pulse point $12_2$.

The one or more transmitted signals 31 may therefore be used for detecting an arterial pulse 2 at different arterial pulse points 12 and for ranging the respective arterial pulse points 12 by measuring the first distance $d_1$ and the second distance $d_2$.

The one or more transmitted signals 31 may therefore be referred to as one or more detecting and ranging signals. In some cases, detecting and ranging signals may include radio detection and ranging (radar), lidar, or other suitable detection and ranging signals based on reflected waves including sound waves, light waves, and the like.

The one or more transmitted signals reflected $21_1$ from the first arterial pulse point $12_1$ may be one or more detecting and ranging pulses. The one or more transmitted signals reflected $21_2$ from the second arterial pulse point $12_2$ may be one or more detecting and ranging pulses.

In FIG. 2A an arterial pulse 2 travels along an artery 10. The one or more transmitted signals, such as the one or more transmitted signals 31 in FIGS. 4A-4C discussed in more detail below, reflected from the first arterial pulse point $12_1$ and one or more transmitted signals 31 reflected from the second arterial pulse point $12_2$ are received separately at different receivers and the first distance $d_1$ to the first arterial pulse point $12_1$ and a second distance $d_2$ to a second arterial pulse point $12_2$ are measured to a different respective receiver.

In FIG. 2B an arterial pulse 2 travels along an artery 10. The one or more transmitted signals 31 reflected from the first arterial pulse point $12_1$ and one or more transmitted signals 31 reflected from the second arterial pulse point $12_2$ are received at the same receiver and the first distance $d_1$ to the first arterial pulse point $12_1$ and a second distance $d_2$ to a second arterial pulse point $12_2$ are measured to the same receiver.

The one or more receivers that receive the one or more transmitted signals 31 reflected from the first arterial pulse point $12_1$ and one or more transmitted signals 31 reflected from the second arterial pulse point $12_2$ may be contactless receivers that do not contact the subject. In this situation, at least a portion of the first distance d1 may be in free space that separates the subject and the receiver. This portion may be a majority of the first distance and may be greater than 5, 20 or 50 cm. Also at least a portion of the second distance d2 may be in free space that separates the subject and the receiver. This portion may be a majority of the second distance and may be greater than 5, 20 or 50 cm.

Referring back to FIG. 1, the method 100 comprises, at block 102, determining an in vivo transit distance D for an arterial pulse 2 between a first arterial pulse point $12_1$ and a second arterial pulse point $12_2$ using a first distance $d_1$ measured to the first arterial pulse point $12_1$ and a second distance $d_2$ measured to a second arterial pulse point $12_2$.

The method 100 comprises, at block 104, determining a transit time T for an arterial pulse 2 between the first arterial pulse point $12_1$ and the second arterial pulse point $12_2$, based on one or more transmitted signals reflected $21_1$ from the first arterial pulse point $12_1$ and from one or more transmitted signals reflected $21_2$ from the second arterial pulse point $12_2$. The transmitted signals may be detecting and ranging wave pulses.

Although it is possible for the arterial pulse of block 102 to be different to the arterial pulse of block 104, it is preferable for the arterial pulse of block 102 to be the same as the arterial pulse of block 104. Block 102 then determines an in vivo transit distance D and block 104 determines a transit time T for the same arterial pulse 2 between two arterial pulse points 12. In some cases, the distance D may be understood as an estimate of arterial travel along artery 10.

The blocks 102, 104 may be performed at one or more processors. Typically blocks 102, 104 are performed at the same processor.

The method 100 may, in some but not necessarily all examples, also comprise additional blocks such as, for example block 106. Some or all of these additional blocks, such as block 106, may be performed at the same processor as block 102 and/or block 104.

The method 100, at block 106, comprises determining a pulse wave velocity (PWV) using the in vivo transit distance D for an arterial pulse 2 between the first arterial pulse point $12_1$ and the second arterial pulse point $12_2$ and the transit time T for the arterial pulse 2 between the first arterial pulse point $12_1$ and the second arterial pulse point $12_2$. The PWV=D/T.

The PWV and/or the pule wave transit time T can be analyzed, for example, over time and, optionally, in response to subject postural changes to assess subject health, for example.

Figure 3:
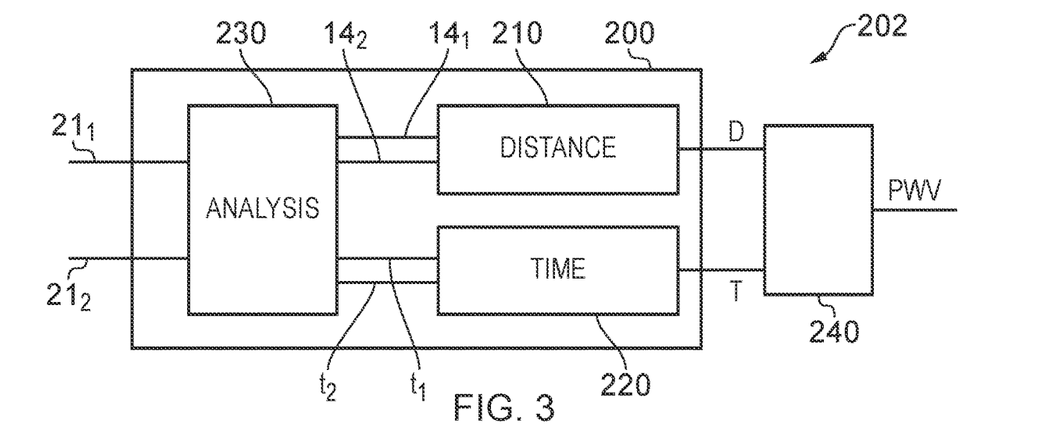
FIG. 3 illustrates a system for performing the method of FIG. 1.

FIG. 3 illustrates a system 200, which may for example be an apparatus or a component of an apparatus, that is configured to perform the method 100.

The system 200 comprises a distance module 210 configured to determine an in vivo transit distance D for an arterial pulse 2 between a first arterial pulse point $12_1$ and a second arterial pulse point $12_2$ when it receives as inputs the first distance $d_1$ measured to the first arterial pulse point $12_1$ and the second distance $d_2$ measured to the second arterial pulse point $12_2$. The distance module 210 may be implemented as a software module and/or a hardware module.

The system 200 comprises a transit time module 220 configured to determine a transit time T for an arterial pulse 2 between the first arterial pulse point $12_1$ and the second arterial pulse point $12_2$ from time information identifying the time difference between when the arterial pulse 2 was at the first arterial pulse point $12_1$ and when the arterial pulse 2 was at the second arterial pulse point $12_2$. The transit time module 220 may be implemented as a software module and/or a hardware module.

The time information identifying the time difference between when the arterial pulse 2 was at the first arterial pulse point $12_1$ and when the arterial pulse 2 was at the second arterial pulse point $12_2$ is based on one or more transmitted signals reflected from the first arterial pulse point $12_1$ and from one or more transmitted signals reflected from the second arterial pulse point $12_2$.

Although the first distance $d_1$ measured to the first arterial pulse point $12_1$ and the second distance $d_2$ measured to a second arterial pulse point $12_2$ may be measured in any suitable way, the first distance $d_1$ may also be measured using the same one or more transmitted signals reflected from the first arterial pulse point $12_1$ and the second distance $d_2$ may be measured using the same one or more transmitted signals reflected from the second arterial pulse point $12_2$.

In this example, but not necessarily all examples, the system 200 comprises an analysis module 230 configured to process transmitted signals reflected from the first arterial pulse point $12_1$ or process information determined from such reflected signals and is also configured to process transmitted signals reflected from the second arterial pulse point $12_2$ or process information determined from such reflected signals.

The analysis module 230 is configured to measure a first time $t_1$ when an arterial pulse 2 is at the first arterial pulse point $12_1$ and the first distance $d_1$ to the first arterial pulse point $12_1$ based on one or more signals $S_1$ that are transmitted signals reflected from the first arterial pulse point $12_1$ or information determined from such reflected signals.

The analysis module 230 is configured to measure a second time $t_2$ when an arterial pulse 2 is at the second arterial pulse point $12_2$ and the second distance $d_2$ to the second arterial pulse point $12_2$ based on one or more signals S2 that are transmitted signals reflected from the second arterial pulse point $12_2$ or information determined from such reflected signals.

The first time and the second time or their difference may be provided as the time information identifying the time difference between when the arterial pulse 2 was at the first arterial pulse point $12_1$ and when the arterial pulse 2 was at the second arterial pulse point $12_2$. The transit time T is the difference between the first time and the second time.

A system 202 comprises system 200 and in addition velocity calculation block 240 which is configured to determine a pulse wave velocity PWV using the in vivo transit distance D for an arterial pulse 2 between the first arterial pulse point $12_1$ and the second arterial pulse point $12_2$ and the transit time T for the arterial pulse 2 between the first arterial pulse point $12_1$ and the second arterial pulse point $12_2$. The PMV=D/T.

Figure 4A:
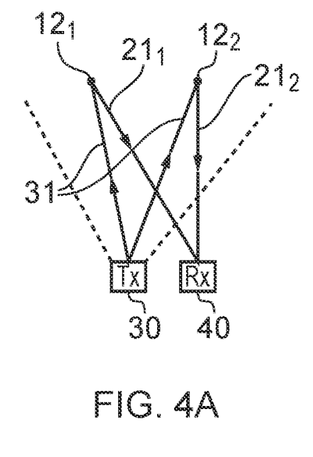
FIGS. 4A to 4C illustrate various transmitter/receiver architectures.
Figure 4B:
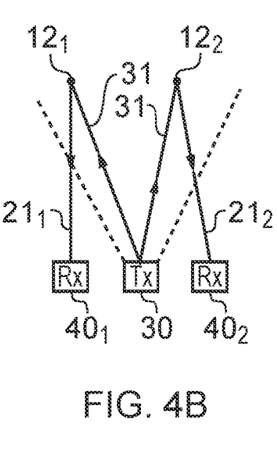
Figure 4C:
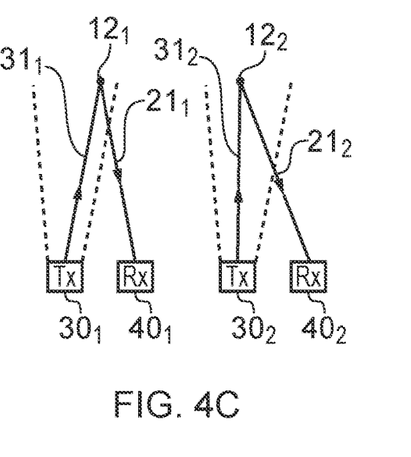

FIGS. 4A to 4C illustrate various transmitter/receiver architectures that comprise one or more transmitters 30 configured to transmit signals 31 that are incident on at least the first arterial pulse point $12_1$ and the second arterial pulse point $12_2$ and one or more receivers 40 configured to receive reflected signals 21 produced when the transmitted signals 31 are reflected from the arterial pulse points 12.

In some, but not necessarily all examples, the one or more transmitters 30 are contactless and/or the one or more receivers 20 are contactless such that they do not contact the subject.

In some, but not necessarily all examples, the one or more transmitters 30 transmit light for example red light and/or infrared light. In some, but not necessarily all examples, the one or more transmitters 30 transmit ultrasound.

In some, but not necessarily all examples, the one or more transmitters 30 transmit detecting and ranging (DAR) wave pulses. Detecting and ranging (DAR) may be understood to include Radio Detecting and Ranging (RADAR) as well as other types of detecting and ranging using other types of propagated waves. For example, the wave pulse may be light, red light and/or infrared light. In some cases, the wave pulse may be ultrasound.

The first roundtrip time $\tau_1$ from a transmitter 30 to the first arterial pulse point $12_1$ and back to the receiver 40 defines a first range $R_1$. $R_1 = \tau_1 * v$, where v is the speed to the transmitted signal 31. The second roundtrip time $\tau_2$ from the same or different transmitter 30 to the second arterial pulse point $12_2$ and back to the same or different receiver 40 defines a second range $R_2$. $R_2 = \tau_2 * v$, where v is the speed of the transmitted signal 31. The different roundtrip times/ranges can be measured in different ways using match filtering, correlation, phase detection etc. The first distance $d_1$ to the first arterial pulse point $12_1$ is half the first range $R_1$. The second distance $d_2$ to the second arterial pulse point $12_2$ is half the second range $R_2$.

Figure 5:
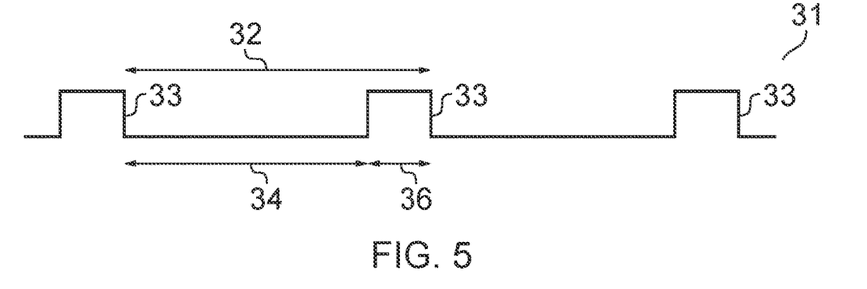
FIG. 5 illustrates an example of a pulsed transmitted signal.

The first time of arrival of the reflected signal 21 reflected from the first arterial pulse point $12_1$ is equal to half the first roundtrip time $\tau_1$ from the transmitter 30 to the first arterial pulse point $12_1$ and back, added to the first time $\tau_1$ when the arterial pulse 2 was at the first arterial pulse point $12_1$. It is therefore possible to determine the first time $t_1$ from the first time of arrival. In some circumstances, for example when the speed of the transmitted signal is very much greater than the pulse wave velocity, the first time $t_1$ may be estimated as the first time of arrival The second time of arrival of the reflected signal 21 reflected from the second arterial pulse point $12_2$ may be equal to half the second roundtrip time $\tau_2$ from the transmitter 30 to the second arterial pulse point $12_2$ and back, added to the second time $t_2$ when the arterial pulse 2 was at the second arterial pulse point $12_2$. It is therefore possible to determine the second time $t_2$ from the second time of arrival. In some circumstances, for example when the speed of the transmitted signal is very much greater than the pulse wave velocity, the second time $t_2$ may be estimated as the second time of arrival The transmitted signal 31 may be a time-variable signal to enable disambiguation of reflected signals 21 from different pulse points. The transmitted signal 31 may be provided as an amplitude modulated wave, for example an amplitude modulated electromagnetic wave (e.g. light) or an amplitude modulated sound wave (e.g. ultrasound). For example, as illustrated in FIG. 5, the transmitted signal 31 may be a pulse signal comprising signal pulses 33 of time duration (width) 36 separated by a time duration 34. The signal pulses 33 may have a fixed width 36 and fixed separation 34, in which case they are periodic with period 32.

The duration 34 may be large enough to prevent cross-talk at the receiver. That is simultaneous reception of different signal pulses 33 reflected from different arterial pulse points.

The duration 34 may be small enough to sample the arterial pulse wave at multiple positions.

In FIG. 4A, a single transmitter 30 produces a spatially broad (wide area-beam) transmitted signal 31 that is incident on both the first arterial pulse point $12_1$ and the second arterial pulse point $12_2$. The reflected signals 21 are received at a single receiver 40.

In FIG. 4B, a single transmitter 30 produces a spatially broad (wide area-beam) transmitted signal 31 that is incident on both the first arterial pulse point $12_1$ and the second arterial pulse point $12_2$. The reflected signals 21 are received at spatially diverse receivers 40. A first reflected signal $21_1$ from the first arterial pulse point $12_1$ is received at a first receiver $40_1$. A second reflected signal $21_2$ from the second arterial pulse point $12_2$ is received at a second receiver $40_2$.

In FIG. 4C, a first transmitter 30 produces a first spatially narrow (narrow area-beam) transmitted signal $31_1$ that is incident on only the first arterial pulse point $12_1$. The first reflected signals $21_1$ produced by the reflection of the first transmitted signals $31_1$ from the first arterial pulse point 12-1 are received at a first receiver $40_1$. A second transmitter 30 produces a second spatially narrow (narrow area-beam) transmitted signal $31_2$ that is incident on only the second arterial pulse point $12_2$. The second reflected signals $21_2$ produced by the reflection of the second transmitted signals $31_2$ from the second arterial pulse point 12-2 are received at a second receiver $40_2$.

In these example, time synchronization occurs as a result of time synchronizing the one or more transmitters and the one or more receivers.

In these examples, only two arterial pulse points 12 are illustrated for clarity of description. However, in other examples there may be more arterial pulse points 12. The architectures illustrated in FIGS. 4A-4C may each be scaled to cover larger areas (more arterial pulse points). Furthermore, the architectures may be mixed such that different groups of arterial pulse points are measured using different architectures. In some examples, an arterial pulse point 12 may be covered by a single architecture. In other examples, an arterial pulse point may be covered by multiple architectures. Where multiple architectures are used, it may be necessary to maintain time synchronization between architectures. Where multiple architectures overlap, it may be necessary to maintain isolation between architectures to prevent cross-talk noise.

In some examples, filtering may be performed on received signals 21 to remove artifacts arising from movement other than an arterial pulse 2. For example, spectral band filtering may be used to bandwidth limit the received signals 21 to only those frequency components associated with an arterial pulse. For example, a bandpass filter may limit the signals to frequency components between 40 and 200 Hz. The filter may be adjustable.

It may also be possible to use filtering (based on the spectral band) or various interference suppression/mitigation techniques to minimize the impact of disturbances such as respiration and gross movement.

Figure 6:
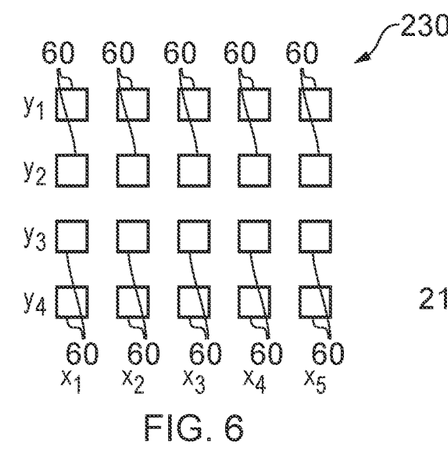
FIG. 6 illustrates an example of operation of an analysis module.

FIG. 6 illustrates operation of an analysis module 230 that is configured to measure a first time $t_1$ when an arterial pulse 2 is at the first arterial pulse point $12_1$ and the first distance $d_1$ to the first arterial pulse point $12_1$ based on one or more signals $S_1$ that are transmitted signals reflected from the first arterial pulse point $12_1$ or information determined from such reflected signals and is configured to measure a second time $t_2$ when the same arterial pulse 2 is at the second arterial pulse point $12_2$ and the second distance $d_2$ to the second arterial pulse point $12_2$ based on one or more signals S2 that are transmitted signals reflected from the second arterial pulse point $12_2$ or information determined from such reflected signals.

The analysis module 230 processes the one or more received reflected signals 21 (from one or more receivers) into multiple bins 60. Each bin 60 is associated with a range R and a time.

The bins 60 in FIG. 6 are arranged in order. Each row is associated with a different sampling time (slow time). Each column is associated with a difference in range/travel time (fast time) for a sample.

The bins 60 are separated in the x-direction by different phases of the same sample (same signal pulse, different ranges).

The bins 60 are separate in the y-direction by different samples reflected with the same range (same range, different sample/time)

The bin value B(x,y) is the signal intensity for a range defined by x and for a time defined by y.

For a given range R, traversing up/down the bins 60 in a column provides a time-domain signal at that range R. The maximum intensity value of one of the bins 60 in a column identifies the time (row) associated with the passage of the arterial pulse 2.

Therefore by identifying maximum intensity bins it is possible to identify arterial pulses. The bin position B(x,y) of maximal intensity determines the Range (x) and the time (y).

In this way it is possible to measure a time $t_n$ when the arterial pulse 2 is at the arterial pulse point $12_n$ and the first distance $d_n$ to the arterial pulse point $12_n$, for each arterial pulse point n.

The transit time T for the arterial pulse 2 between the different arterial pulse points 12 is determined from the differences in the time $t_n$ from those arterial pulse points.

Where the transmitted signal 31 is a pulsed signal each sample/time (y) is associated with a different one of a plurality of sequentially transmitted detecting and ranging pulses 33 (e.g. radar pulses). The duration 36 and separation 34 of the pulses 33 are configured to spatially resolve the sampled arterial pulse points 12, such that each bin 60 is associated with only a single arterial pulse point (x).

Each bin 60 is associated with one of a plurality of samples/times (y) and is associated with one of a multiplicity of short (fast)-time periods (x), for different trip times/ranges, within a long (slow) time period (sample duration 36) at the associated time (sample time). Each sample/time is associated with a different one of a plurality of sequentially transmitted detecting and ranging pulses 33 (e.g. radar pulses). The duration 34 is configured to spatially resolve the first arterial pulse point $12_1$ and the second arterial pulse point $12_2$, such that each bin 60 is associated with only a single arterial pulse point.

The analysis module may therefore enable a method for determining pulse wave velocity (PWV) comprising: processing the results of contactless pulsed detecting and ranging (e.g. radar) detection into multiple range bins 60 for each detecting and ranging pulse 33 (e.g. radar pulse); using the range bins 60 to determine an in vivo distance D between pulse points 12 at different ranges; determining a pulse transit time T between the pulse points; and determining a pulse wave velocity PWV using the in vivo distance between the pulse points 12 and the pulse transit time T between the pulse points 12.

Figure 7:
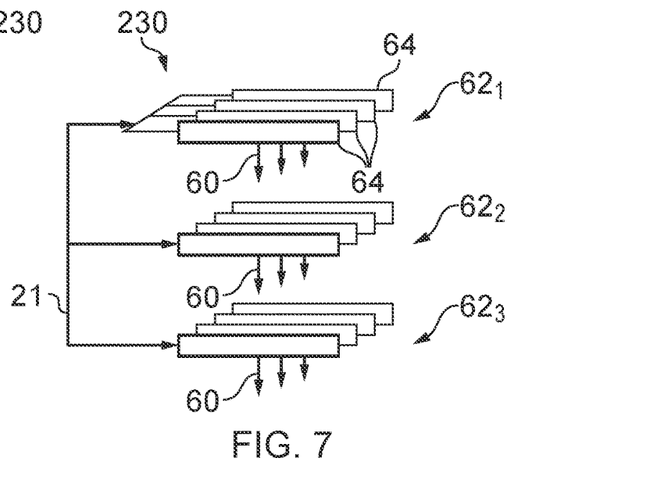
FIG. 7 illustrates an example of an implementation of analysis module using matched filters.

FIG. 7 illustrates an example of an analysis module 230. The analysis module 230 processes the one or more received reflected signals 21 (from one or more receivers) into multiple bins 60. Each bin 60 is associated with a range R and a time.

The analysis module comprises a plurality of groups 62 of matched filters 64. Each group 62 comprises multiple matched filters 64. A matched filter receives the reflected signals 21 and produces a bin 60.

The delay between the groups 62 of matched filters corresponds to the slow time (different y). Each group 62 of matched filters produces a row of bins 60.

The delay within the groups of matched filters between the matched filters 64 of a group corresponds to the fast time (different x). Each matched filter 64 within a group produces a bin 60 at a different bin within the row.

A (time) bandwidth of a matched filter 64 wide enough so that different arterial pulse points for the same sample fall into different bins 60 in the same row. The signal pulse needs to be sufficiently narrow in time (wide band in frequency e.g. ⅗ GHz) to provide a desired spatial/distance accuracy (e.g. 10/5 cm). The spatial resolution is inversely proportional to the pulse bandwidth.

In some circumstances the first distance $d_1$ measured to the first arterial pulse point $12_1$ and the second distance $d_2$ measured to a second arterial pulse point $12_2$ may be converted to an in vivo transit distance for an arterial pulse 2 between a first arterial pulse point $12_1$ and a second arterial pulse point $12_2$ using simple trigonometry when the in vivo distance is the same as or approximates to a straight line distance between the first arterial pulse point and the second arterial pulse point.

However, a more general solution is desirable to account for other situations, for example, when the in vivo distance D does not approximate to a straight line distance between the first arterial pulse point and the second arterial pulse point.

Figure 8:
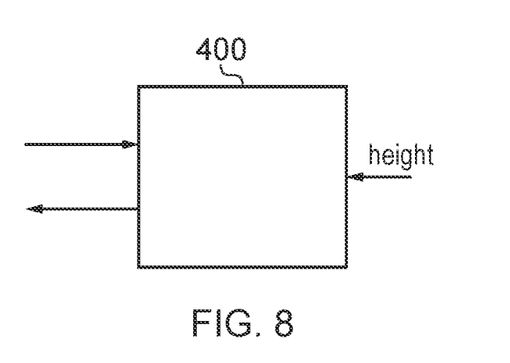
FIG. 8 illustrates an example of a module for determining an in vivo distance from distances measured to the arterial pulse points.

FIG. 8 illustrates a module 400 for determining an in vivo distance D from distances d measured to the arterial pulse points 12. The module 400 may be part of the distance module 210 illustrated in FIG. 3, for example.

The module 400 receives from the analysis module 230 at least a collection of different distances {d} measured to different arterial pulse points 12.

The module 400 is configured to map the different arterial pulse points 12 to anatomical locations on the subject.

From the anatomical locations of the pulse points 12, the in vivo transit distance D for an arterial pulse 2 between the different measured arterial pulse points is determined from a look-up table that records in vivo transit distances D for an arterial pulse 2 between different anatomical locations.

For example, the collection of pulse points and optionally the intensities of signal measured at the pulse points 12, forms a constellation that when re-scaled to account for a height of the subject and re-oriented to match a reference constellation of anatomical pulse points, allows the measured pulse points 12 to be mapped to the anatomical pulse points and the reference in vivo transit distance D taken from the reference constellation. The reference in vivo transit distance D is then re-scaled to account for a height of the subject to obtain an in vivo transit distance for the subject.

Figure 9:
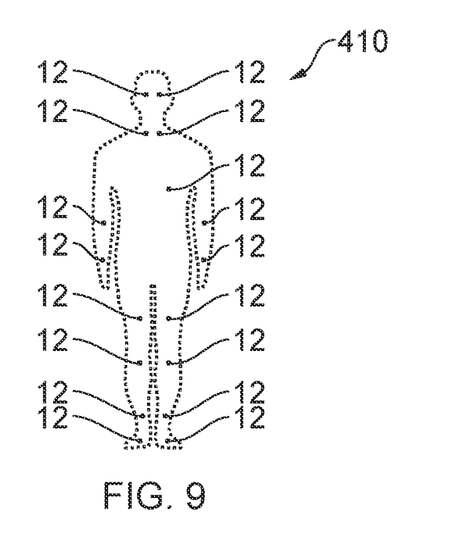
FIG. 9 illustrates a constellation of measured pulse points.

The constellation creates a "stick figure" 410, as illustrated in FIG. 9, for the subject's body represented by the measured pulse points 12. In this example, but not necessarily all examples, the subject is a human and a reference constellation of anatomical pulse points 12 is shown. The pulse points used may, for example, include one or more of the temporal pulse points, the carotid pulse points, the apical pulse point, the brachial pulse points, the radial pulse points, the femoral pulse points, the popliteal pulse points, the posterior tibial pulse points and the pedal pulse points.

This approach allows a femoral arterial pulse point and a radial arterial pulse point to be identified and the in vivo distance via the shoulder to be determined.

Figure 10A:
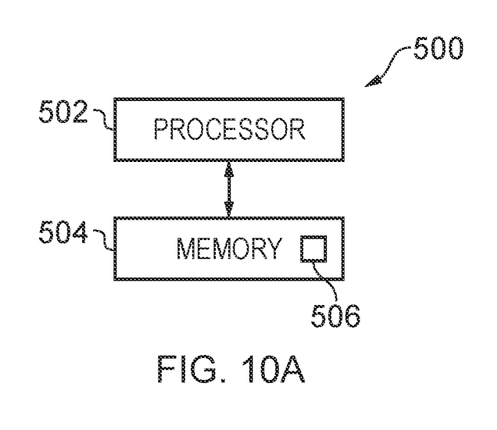
FIG. 10A illustrates an example of a controller.

FIG. 10A illustrates an example of a controller 500 that may be configured to perform any one or more of the processes described. It may for example perform the method 100 or any block of that method. It may, for example, perform the function of any system or module described.

The controller 500 may therefore be configured to determine an in vivo transit distance D for an arterial pulse 2 between a first arterial pulse point $12_1$ and a second arterial pulse point $12_2$ using a first distance $d_1$ measured to the first arterial pulse point $12_1$ and a second distance $d_2$ measured to a second arterial pulse point $12_2$; and to determine a transit time T for an arterial pulse 2 between the first arterial pulse point $12_1$ and the second arterial pulse point $12_2$, based on one or more transmitted signals 31 reflected from the first arterial pulse point $12_1$ and from one or more transmitted signals 31 reflected from the second arterial pulse point $12_2$.

Implementation of a controller 500 may be as controller circuitry. The controller 500 may be implemented in hardware alone, have certain aspects in software including firmware alone or can be a combination of hardware and software (including firmware).

As illustrated in FIG. 10A the controller 500 may be implemented using instructions that enable hardware functionality, for example, by using executable instructions of a computer program 506 in a general-purpose or special-purpose processor 502 that may be stored on a computer readable storage medium (disk, memory etc) to be executed by such a processor 502.

The processor 502 is configured to read from and write to the memory 504. The processor 502 may also comprise an output interface via which data and/or commands are output by the processor 502 and an input interface via which data and/or commands are input to the processor 502.

The memory 504 stores a computer program 506 comprising computer program instructions (computer program code) that controls the operation of the apparatus 500 when loaded into the processor 502. The computer program instructions, of the computer program 506, provide the logic and routines that enables the apparatus to perform the methods illustrated in FIGS. 1, 6, 7 & 8. The processor 502 by reading the memory 504 is able to load and execute the computer program 506.

The apparatus 500 therefore comprises:
at least one processor 502; and
at least one memory 504 including computer program code
the at least one memory 504 and the computer program code configured to, with the at least one processor 502, cause the apparatus 500 at least to perform:
causing determining of an in vivo transit distance D for an arterial pulse 2 between a first arterial pulse point $12_1$ and a second arterial pulse point $12_2$ using a first distance $d_1$ measured to the first arterial pulse point $12_1$ and a second distance $d_2$ measured to a second arterial pulse point 122; and causing determining a transit time T for an arterial pulse 2 between the first arterial pulse point $12_1$ and the second arterial pulse point $12_2$, based on one or more transmitted signals 31 reflected from the first arterial pulse point $12_1$ and from one or more transmitted signals 31 reflected from the second arterial pulse point 122. The transmitted signals may be detecting and ranging wave pulses.

Figure 10B:
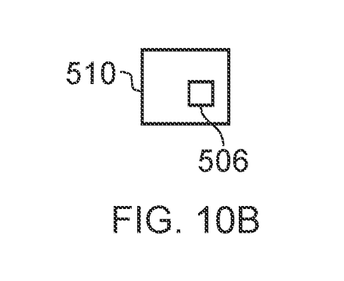
FIG. 10B illustrates an example of a computer program.

As illustrated in FIG. 10B, the computer program 506 may arrive at the apparatus 500 via any suitable delivery mechanism 510. The delivery mechanism 510 may be, for example, a non-transitory computer-readable storage medium, a computer program product, a memory device, a record medium such as a compact disc read-only memory (CD-ROM) or digital versatile disc (DVD), an article of manufacture that tangibly embodies the computer program 506. The delivery mechanism may be a signal configured to reliably transfer the computer program 506. The apparatus 500 may propagate or transmit the computer program 506 as a computer data signal.

Although the memory 504 is illustrated as a single component/circuitry it may be implemented as one or more separate components/circuitry some or all of which may be integrated/removable and/or may provide permanent/semi-permanent/dynamic/cached storage.

Although the processor 502 is illustrated as a single component/circuitry it may be implemented as one or more separate components/circuitry some or all of which may be integrated/removable. The processor 502 may be a single core or multi-core processor.

References to 'computer-readable storage medium', 'computer program product', 'tangibly embodied computer program' etc. or a 'controller', 'computer', 'processor' etc. should be understood to encompass not only computers having different architectures such as single/multi-processor architectures and sequential (Von Neumann)/parallel architectures but also specialized circuits such as field-programmable gate arrays (FPGA), application specific circuits (ASIC), signal processing devices and other processing circuitry. References to computer program, instructions, code etc. should be understood to encompass software for a programmable processor or firmware such as, for example, the programmable content of a hardware device whether instructions for a processor, or configuration settings for a fixed-function device, gate array or programmable logic device etc.

As used in this application, the term 'circuitry' refers to all of the following:
(a) hardware-only circuit implementations (such as implementations in only analog and/or digital circuitry) and
(b) to combinations of circuits and software (and/or firmware), such as (as applicable): (i) to a combination of processor(s) or (ii) to portions of processor(s)/software (including digital signal processor(s)), software, and memory(ies) that work together to cause an apparatus, such as a mobile phone or server, to perform various functions and
(c) to circuits, such as a microprocessor(s) or a portion of a microprocessor(s), that require software or firmware for operation, even if the software or firmware is not physically present.

This definition of 'circuitry' applies to all uses of this term in this application, including in any claims. As a further example, as used in this application, the term "circuitry" would also cover an implementation of merely a processor (or multiple processors) or portion of a processor and its (or their) accompanying software and/or firmware. The term "circuitry" would also cover, for example and if applicable to the particular claim element, a baseband integrated circuit or applications processor integrated circuit for a mobile phone or a similar integrated circuit in a server, a cellular network device, or other network device.

The blocks illustrated in the FIGS. 1, 6, 7 & 8 may represent steps in a method and/or sections of code in the computer program 506. The illustration of a particular order to the blocks does not necessarily imply that there is a required or preferred order for the blocks and the order and arrangement of the block may be varied. Furthermore, it may be possible for some blocks to be omitted.

Where a structural feature has been described, it may be replaced by means for performing one or more of the functions of the structural feature whether that function or those functions are explicitly or implicitly described.

Consequently an apparatus 200 may comprise: means for determining an in vivo transit distance D for an arterial pulse 2 between a first arterial pulse point $12_1$ and a second arterial pulse point 122 using a first distance $d_1$ measured to the first arterial pulse point $12_1$ and a second distance $d_2$ measured to a second arterial pulse point $12_2$; and means for determining a transit time T for an arterial pulse 2 between the first arterial pulse point $12_1$ and the second arterial pulse point $12_2$, based on one or more transmitted signals 31 reflected from the first arterial pulse point 121 and from one or more transmitted signals 31 reflected from the second arterial pulse point 122. The one or more transmitted signals 31 may be one or more detecting and ranging wave pulses.

The term 'comprise' is used in this document with an inclusive not an exclusive meaning. That is any reference to X comprising Y indicates that X may comprise only one Y or may comprise more than one Y. If it is intended to use 'comprise' with an exclusive meaning then it will be made clear in the context by referring to "comprising only one" or by using "consisting".

In this brief description, reference has been made to various examples. The description of features or functions in relation to an example indicates that those features or functions are present in that example. The use of the term 'example' or 'for example' or 'may' in the text denotes, whether explicitly stated or not, that such features or functions are present in at least the described example, whether described as an example or not, and that they can be, but are not necessarily, present in some of or all other examples. Thus 'example', 'for example' or 'may' refers to a particular instance in a class of examples. A property of the instance can be a property of only that instance or a property of the class or a property of a sub-class of the class that includes some but not all of the instances in the class. It is therefore implicitly disclosed that a feature described with reference to one example but not with reference to another example, can where possible be used in that other example but does not necessarily have to be used in that other example.

Although embodiments of the present innovation have been described in the preceding paragraphs with reference to various examples, it should be appreciated that modifications to the examples given can be made without departing from the scope of the innovation as claimed.

Features described in the preceding description may be used in combinations other than the combinations explicitly described.

Although functions have been described with reference to certain features, those functions may be performable by other features whether described or not.

Although features have been described with reference to certain embodiments, those features may also be present in other embodiments whether described or not.

Whilst endeavoring in the foregoing specification to draw attention to those features of the innovation believed to be of particular importance it should be understood that the Applicant claims protection in respect of any patentable feature or combination of features hereinbefore referred to and/or shown in the drawings whether or not particular emphasis has been placed thereon.

The invention claimed is:

1. A method, comprising:
   at least one transmitter transmitting a sequence of wave pulses;
   a radar receiver receiving reflections of the wave pulses, the radar receiver including a plurality of filters (i) spectrally filtering the reflections to cause corresponding filtered signals to be limited to spectral components associated with an arterial pulse and (ii) sampling the filtered signals at different delay times with respect to corresponding ones of the wave pulses to generate corresponding groups of samples; and
   at a processor connected to the at least one transmitter and the radar receiver, the processor determining an in vivo transit distance and a transit time for the arterial pulse between a first arterial pulse point and a different second arterial pulse point; and
   wherein said determining comprises:
      in the corresponding groups of samples, the processor identifying at least a first sample corresponding to the first arterial pulse point and a second sample corresponding to the second arterial pulse point;
      based on the delay times of the first and second samples with respect to the corresponding ones of the wave pulses, the processor determining first and second distances, the first distance being a distance from the radar receiver to the first arterial pulse point, the second distance being a distance from the radar receiver to the second arterial pulse point;
      based on the first and second distances, the processor determining the in vivo transit distance; and
      based on a relative time delay between the first and second samples, the processor determining the transit time.

2. The method as claimed in claim 1, further comprising the processor processing the reflections into multiple bins, wherein each bin is associated with a corresponding range and a corresponding time.

3. The method as claimed in claim 2, further comprising the processor identifying different ones of the bins for different arterial pulse points and using the identified bins to measure distances from the radar receiver to the different arterial pulse points based on the corresponding ranges associated with the identified bins.

4. The method as claimed in claim 1, further comprising the processor selecting a wave-pulse duration to spatially resolve the first arterial pulse point and the second arterial pulse point.

5. The method as claimed in claim 1, comprising the processor determining an arterial-pulse wave velocity using the in vivo transit distance and the transit time.

6. The method as claimed in claim 1, wherein the at least one transmitter comprises a wide beam contactless transmitter or multiple narrower beam contactless transmitters.

7. The method as claimed in claim 3, further comprising:
   based on a collection of the distances measured to the different arterial pulse points, the processor mapping the different arterial pulse points to corresponding anatomical locations; and
   the processor determining the in vivo transit distance for the arterial pulse by looking up a value of the in vivo transit distance for a pair of the corresponding anatomical locations, said pair including a first anatomical location mapped to the first arterial pulse point and a second anatomical location mapped to the different second arterial pulse point.

8. The method as claimed in claim 7, further comprising:
the processor forming a subject constellation based on a collection of the different arterial pulse points and of values of the identified bins;
the processor re-scaling and re-orienting the subject constellation to match a reference constellation; and
the processor determining the value of the in vivo transit distance based on the reference constellation.

9. The method as claimed in claim 1, wherein the at least one transmitter transmits the sequence of wave pulses to enable disambiguation of the reflections from the first and second arterial pulse points.

10. The method as claimed in claim 1, wherein the at least one transmitter transmits the sequence of wave pulses such that any two consecutive wave pulses therein have a fixed time separation.

11. An apparatus, comprising:
a transmitter that transmits a sequence of wave pulses;
a radar receiver that receives reflections of the wave pulses, the radar receiver including a plurality of filters that spectrally filter the reflections to cause corresponding filtered signals to be limited to spectral components associated with an arterial pulse and sample the filtered signals at different delay times with respect to corresponding ones of the wave pulses to generate corresponding groups of samples;
at least one processor; and
at least one memory including computer program code, the at least one memory and the computer program code, with the at least one processor, cause the apparatus at least to:
in the corresponding groups of samples, identify at least a first sample corresponding to a first arterial pulse point and a second sample corresponding to a different second arterial pulse point;
based on the delay times of the first and second samples with respect to the corresponding ones of the wave pulses, determine first and second distances, the first distance being a distance from the radar receiver to the first arterial pulse point, the second distance being a distance from the radar receiver to the second arterial pulse point;
based on the first and second distances, determine an in vivo transit distance for the arterial pulse between the first and second arterial pulse points; and
based on a relative time delay between the first and second samples, determine a transit time for the arterial pulse between the first and second arterial pulse points.

12. The apparatus as claimed in claim 11, wherein the at least one memory and the computer program code, with the at least one processor, cause the apparatus at least to:
process the reflections into multiple bins, wherein each bin is associated with a corresponding range and a corresponding time; and
identify different ones of the bins for different arterial pulse points and using the identified bins to measure distances from the radar receiver to the different arterial pulse points based on the corresponding ranges associated with the identified bins.

13. The apparatus as claimed in claim 12, wherein the at least one memory and the computer program code, with the at least one processor, cause the apparatus at least to:
based on a collection of the distances measured to the different arterial pulse points, map the different arterial pulse points to corresponding anatomical locations; and
determine the in vivo transit distance for the arterial pulse by looking up a value of the in vivo transit distance for a pair of the corresponding anatomical locations, said pair including a first anatomical location mapped to the first arterial pulse point and a second anatomical location mapped to the different second arterial pulse point.

14. The apparatus as claimed in claim 13, wherein the at least one memory and the computer program code, with the at least one processor, cause the apparatus at least to:
form a subject constellation based on a collection of the different arterial pulse points and of values of the identified bins;
re-scale and re-orient the subject constellation to match a reference constellation; and
determine the value of the in vivo transit distance based on the reference constellation.

15. The apparatus as claimed in claim 11, wherein the at least one transmitter transmits the sequence of wave pulses to enable disambiguation of the reflections from the first and second arterial pulse points.

16. The apparatus as claimed in claim 11, wherein the at least one transmitter transmits the sequence of wave pulses such that any two consecutive wave pulses therein have a fixed time separation.

* * * * *